United States Patent [19]

Sakamoto et al.

[11] 4,166,865
[45] Sep. 4, 1979

[54] MACROTETROLIDE ANIMAL GROWTH PROMOTOR

[75] Inventors: Koji Sakamoto; Takeshi Asano, both of Takasaki; Kazuo Mizuochi, Tokyo; Kanemichi Sasaki, Koshigaya; Kouji Hasegawa, Omiya, all of Japan

[73] Assignees: Chugai Seiyaku Kabushiki Kaisha; Nippon Kayaku Kabushiki Kaisha, both of Tokyo, Japan

[21] Appl. No.: 933,912

[22] Filed: Aug. 15, 1978

[30] Foreign Application Priority Data

Aug. 18, 1977 [JP] Japan .................................. 52-98996

[51] Int. Cl.² ............................................. A61K 31/34
[52] U.S. Cl. .................................................... 424/285
[58] Field of Search ........................................ 424/285

[56] References Cited

U.S. PATENT DOCUMENTS 3,777,023  12/1973  Sagawa et al. .................. 424/219

OTHER PUBLICATIONS

Chemical Abstracts, vol. 64, (1966), p. 20035b.
Chemical Abstracts, vol. 84, (1976), p. 87878y.

*Primary Examiner*—V. D. Turner

[57] ABSTRACT

A method for promoting the growth of domestic animals which comprises administering one or more kinds of macrotetrolide antibiotic substances represented by the general formula

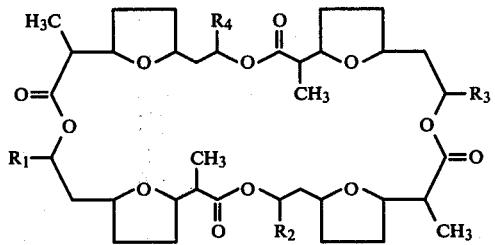

wherein $R_1$, $R_2$, $R_3$ and $R_4$ each represents a lower alkyl group, to the animals.

10 Claims, No Drawings

MACROTETROLIDE ANIMAL GROWTH PROMOTOR

This invention relates to a method for promoting the growth of domestic animals. More particularly, it relates to a method for promoting the growth of domestic animals which comprises administering one or more kinds of macrotetrolide antibiotic substances represented by the general formula (I)

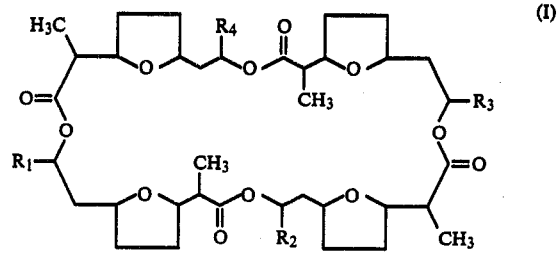

wherein $R_1$, $R_2$, $R_3$ and $R_4$ each represents a lower alkyl group, to the animals.

The present inventors have extensively studied the method for promoting the growth of domestic animals and, as the result, have found that macrotetrolide antibiotic substances represented by the above-mentioned general formula (I) exhibit an excellent growth promoting effect when administered to domestic animals.

This invention has been accomplished on the basis of this finding.

It is an object of this invention to provide a novel method for promoting the growth of domestic animals.

Other objects and advantages of this invention will be apparent from the description given below.

The macrotetrolide antibiotic substances represented by general formula (I), used in this invention, are disclosed compounds referred to in, for example, Helvetica Chimica Acta, 38, 1445–1448 (1955) and ibid. 45, 129–138, 620–630 (1962). They can be produced by cultivating *Streptomyces aureus* (FERM-P No. 233) in a nutrient medium of (cf. Japanese Patent Publication No. 45597/1974)and are known as insecticidal and miticidal agent (U.S. Pat. No. 3777023).

Depending upon the method of production and purification, these antibiotic substances sometimes involve various substances of the same chemical formula but of slightly different physical and chemical properties and therefore considered stereoisomers. In this invention, all these stereoisomers can be used without any discrimination.

Typical compounds represented by general formula (I) are listed in Table 1.

Table 1

| Compound No. | 1 | 2 | 3 | 4 | 5 |
|---|---|---|---|---|---|
| Name | nonactin | monactin | dinactin | trinactin | tetranactin |
| Substituent | | | | | |
| $R_1$ | $CH_3$ | $C_2H_5$ | $C_2H_5$ | $C_2H_5$ | $C_2H_5$ |
| $R_2$ | $CH_3$ | $CH_3$ | $C_2H_5$ | $C_2H_5$ | $C_2H_5$ |
| $R_3$ | $CH_3$ | $CH_3$ | $CH_3$ | $C_2H_5$ | $C_2H_5$ |
| $R_4$ | $CH_3$ | $CH_3$ | $CH_3$ | $CH_3$ | $C_2H_5$ |
| mp (°C.) | 148–149 | 63–64 | 73–74 | 79–80 | 105-106 |

The compounds of the table have an acute oral toxicity ($LD_{50}$) of 25,000 mg/kg or above for mouse, 2,500 mg/kg or above for rat and 2,000 mg/kg or above for quail. These values indicate the extremely low toxicity of these compounds and their very high safety.

The macrotetrolide antibiotic substances obtainable by cultivating *Streptomyces aureus* and represented by the aforementioned general formula (I) are usually in the form of mixture of which main components are dinactin, trinactin and/or tetranactin. This type of mixtures are known under the general name of polynactin complex.

Preferable dose of the macrotetrolide antibiotic substance represented by general formula (I) is 0.01–100 mg/day per 1 kg of the body weight of domestic animal.

The domestic animals to which the growth promotion method of this invention can be applied include, for example, ruminants such as cattle, sheep, etc., as well as swine.

The growth promotion method of this invention is preferably carried out by adding the macrotetrolide antibiotic substance of general formula (I) itself or its mixture with a physiologically harmless solid or liquid carrier to the feed or drinking water for domestic animals. Examples of said solid carrier herein used include wheat meal, soybean meal, defatted rice bran, corn starch, calcium carbonate, talc, kaolinite, chalk, diatomaceous earth and the like. Examples of said liquid carrier include water, isotonic sodium chloride solution and the like. Besides above, adjuvants or additives such as emulsifier, dispersant, suspension stabilizer, wetting agent and the like may also be added if necessary.

Among the various formulations and dosages allowable, it is most practical and economical to incorporate a powdery active ingredient compound of this invention into the feed in a proportion of 0.5–1,000 ppm and administer it to animals continuously.

It is also permissible to mix the antibiotic substance with a carrier, make the mixture into a preparation such as tablet, granule, pellet or bolus, and give it to animals directly.

The excellent effect brought about by the growth promotion method of this invention will be illustrated by reference to the following experimental examples.

EXPERIMENTAL EXAMPLE 1

(1) Procedure of Experiment

Male Corriedale sheeps, 3 months old, were raised for 10 weeks with the fundamental feed shown in Table 2 to which polynactin complex had previously been added in varied proportions.

The animals were divided into 5 groups, each group comprising 10 heads. Concentrations of polynactin complex (10% dinactin, 40% trinactin and 50% tetranactin) in the feeds given to individual groups were 0, 10, 50, 100 and 1000 ppm. During the experiment, body weights of the animals were measured at intervals of 2 weeks. Feed conversion was calculated from feed intake and body weight gain.

Table 2

| Formulation of feed (%) | |
|---|---|
| Corn | 40 |
| Wheat bran | 27 |
| Alfalfa meal | 20 |
| Soybean meal | 10 |
| $Ca_3(PO_4)_2$ | 2 |
| Sodium chloride | 0.5 |
| Vitamin A, D, E mixture | 0.2 |
| Vitamin B complex | 0.2 |
| Minerals | 0.1 |

Table 2-continued

| Formulation of feed (%) | |
|---|---|
| | 100.0 |

(2) Results of Experiment

As shown in Table 3, the groups administrered with polynactin complex are evidently superior in growth to the group not administered with it. As shown in Table 4, polynactin complex greatly improves feed conversion.

Table 3.

| | Growth (kg) | | | | | |
|---|---|---|---|---|---|---|
| Week | 0 | 2 | 4 | 6 | 8 | 10 |
| Concentration (ppm) | | | | | | |
| 0 | 28.5 | 30.2 | 33.5 | 36.2 | 38.1 | 41.2 |
| 10 | 27.9 | 31.4 | 35.4 | 38.5 | 41.2 | 45.8 |
| 50 | 28.2 | 31.8 | 34.3 | 38.1 | 41.0 | 44.3 |
| 100 | 28.1 | 31.6 | 36.0 | 37.9 | 42.0 | 45.5 |
| 1000 | 28.0 | 32.0 | 35.3 | 38.4 | 41.9 | 46.2 |

Table 4

| | Feed conversion (10 weeks) | | |
|---|---|---|---|
| Concentration (ppm) | a. Feed intake (kg/head) | b. Body weight gain (kg/head) | Feed conversion (a/b) |
| 0 | 102.0 | 12.7 | 8.0 |
| 10 | 112.8 | 17.9 | 6.3 |
| 50 | 106.3 | 16.1 | 6.6 |
| 100 | 111.8 | 17.4 | 6.4 |
| 1000 | 111.6 | 18.2 | 6.1 |

EXPERIMENTAL EXAMPLE 2

(1) Procedure of Experiment

Young LH pigs, about 3 weeks old, were raised for 18 weeks with the fundamental feeds shown in Table 5 to which polynactin complex had previously been added in varied proportion. Synthetic milk A as shown in Table 5 was given during 3 weeks after the start of experiment, synthetic milk B as shown in Table 5 was given during the subsequent 5 weeks, and the fattening ration as shown in Table 6 was given during the subsequent 10 weeks.

The animals were divided into 5 groups, each group comprising 10 heads. Concentrations of polynactin complex (10% dinactin, 40% trinactin and 50% tetranactin) in the feeds given to individual groups were 0, 10, 50, 100, and 1000 ppm.

During the experiment, body weights of the animals were measured at intervals of 2 weeks. Feed conversion was calculated from feed intake and body weight gain.

Table 5

| | Synthetic milk A | Synthetic Milk B |
|---|---|---|
| Wheat meal | 37.1 | 48.1 |
| Corn starch | 15 | 15 |
| Soybean meal | 10 | 11.5 |
| Fish meal | 7 | 8.5 |
| Dried skim milk | 30 | 15 |
| Micro additives | 0.9 | 1.9 |
| Total | 100 | 100 |

Table 6

| | Fattening ratio |
|---|---|
| Corn | 76.0 |
| Soybean meal | 14.2 |
| Fish meal | 5.5 |
| Alfalfa meal | 2.5 |
| Sodium Chloride | 0.5 |
| Calcium carbonate | 0.4 |
| Calcium secondary phosphate | 0.4 |
| Vitamin mineral premix | 0.5 |
| Total | 100 |

(2) Results of Experiment

Regarding growth, the groups administered with polynactin complex are evidently superior to the group not administered with it, as shown in Table 7. The groups administered with polynactin complex are much improved in feed conversion rate as shown in Table 8.

Table 7.

| | Growth (kg) | | | | | | | | | |
|---|---|---|---|---|---|---|---|---|---|---|
| Week | 0 | 2 | 4 | 6 | 8 | 10 | 12 | 14 | 16 | 18 |
| Concentration (ppm) | | | | | | | | | | |
| 0 | 5.4 | 7.7 | 14.7 | 24.3 | 32.6 | 44.5 | 58.8 | 69.5 | 80.1 | 89.6 |
| 10 | 5.3 | 8.7 | 16.2 | 27.1 | 36.1 | 52.8 | 68.7 | 80.1 | 90.3 | 101.2 |
| 50 | 5.3 | 8.9 | 17.1 | 27.6 | 37.1 | 53.1 | 67.9 | 81.1 | 91.2 | 100.4 |
| 100 | 5.4 | 8.8 | 17.6 | 28.1 | 38.2 | 54.6 | 70.3 | 82.6 | 92.1 | 101.5 |
| 1000 | 5.3 | 9.2 | 17.5 | 28.2 | 39.7 | 55.9 | 72.7 | 85.3 | 93.6 | 103.5 |

Table 8

| | Feed conversion (18 weeks) | | |
|---|---|---|---|
| Concentration (ppm) | a. Feed intake (kg/head) | b. Body weight gain (kg/head) | Feed conversion (a/b) |
| 0 | 232.0 | 84.2 | 2.76 |
| 10 | 231.1 | 95.9 | 2.41 |
| 50 | 222.5 | 95.1 | 2.34 |
| 100 | 223.9 | 96.1 | 2.33 |
| 1000 | 227.8 | 98.2 | 2.32 |

EXPERIMENTAL EXAMPLE 3

(1) Procedure of Experiment

Holstein steer, 7 months old, were raised for 6 months with the fundamental feed shown in Table 9 to which polynactin complex had previously been added in varied proportion.

The animals were divided into 4 groups, each group comprising 5 heads. Concentrations of polynactin complex (3% dinactin, 7% trinactin and 90% tetranactin) in the feeds given to individual groups were 0, 1, 10 and 100 ppm.

During the experiment, body weights of the animals were measured at intervals of one month. Feed conversion rate was claculated from feed intake and body weight gain.

Table 9.

| Formulation of feed (%) | |
| --- | --- |
| Corn | 19 |
| Wheat bran | 27 |
| Soybean meal | 6 |
| Mollasses | 6 |
| Sodium chloride | 1 |
| Vitamin A, D, E mixture | 0.05 |
| Milo | 18 |
| Defatted rice bran | 13 |
| Linseed meal | 8 |
| Calcium carbonate | 1.5 |
| Calcium phosphate | 0.4 |
| Mineral mixture | 0.05 |
| Total | 100 |

(2) Results of Experiment

Regarding growth, the groups administered with polynactin complex are evidently superior to the group not administered with it, as shown in Table 10. The groups administered with polynactin complex are much improved in feed conversion as shown in Table 11.

Table 10.

| Concentration (ppm) | Growth (kg) | | | | | | |
| --- | --- | --- | --- | --- | --- | --- | --- |
| Month | 0 | 1 | 2 | 3 | 4 | 5 | 6 |
| 0 | 241 | 278 | 317 | 366 | 408 | 430 | 468 |
| 1 | 240 | 284 | 328 | 372 | 414 | 439 | 475 |
| 10 | 236 | 285 | 330 | 381 | 417 | 449 | 481 |
| 100 | 231 | 283 | 326 | 378 | 429 | 438 | 473 |

Table 11

| Concentration (ppm) | Feed conversion | | |
| --- | --- | --- | --- |
| | a. Feed intake (kg/head) | b. Body weight gain (kg/head) | Feed conversion (a/b) |
| 0 | 1717 | 227 | 7.56 |
| 1 | 1638 | 235 | 6.97 |
| 10 | 1668 | 245 | 6.81 |
| 100 | 1634 | 242 | 6.75 |

EXPERIMENTAL EXAMPLE 4

(1) Procedure of Experiment

Male Corriedale sheeps, 3 months old, were raised for 5 weeks with the fundamental feed shown in Table 2 to which 50 ppm of nonactin, monactin, dinactin, trinactin or tetranactin, each alone, had previously been added.

The animals were divided into 6 groups, each group comprising 5 heads. One of the groups was control to which no agent was administered. During the experiment, body weights of the animals were measured at intervals of one week. Feed conversion was calculated from feed intake and body weight gain.

(2) Results of Experiment

The groups administered with nonactin, monactin, dinactin, trinactin or tetranactin, each alone, were evidently superior in growth to the group not administered, as shown in Table 12. These groups were also much improved in feed conversion as shown in Table 13.

Table 12.

| Additive | Growth (kg) | | | | | |
| --- | --- | --- | --- | --- | --- | --- |
| Week | 0 | 1 | 2 | 3 | 4 | 5 |
| None | 26.3 | 27.6 | 28.0 | 29.4 | 31.3 | 32.1 |
| Nonactin | 27.1 | 28.8 | 30.3 | 31.5 | 32.6 | 33.7 |
| Monactin | 26.1 | 28.3 | 29.9 | 31.9 | 32.8 | 33.1 |
| Dinactin | 27.2 | 29.4 | 31.5 | 32.8 | 33.7 | 34.6 |
| Trinactin | 26.7 | 28.5 | 30.7 | 31.0 | 33.5 | 34.2 |
| Tetranactin | 25.4 | 27.9 | 28.4 | 29.6 | 31.2 | 32.8 |

Table 13

| Additive | Feed conversion (5 weeks) | | |
| --- | --- | --- | --- |
| | a. Feed intake (kg/head) | b. Body weight gain (kg/head) | Feed conversion (a/b) |
| None | 42.9 | 5.8 | 7.4 |
| Nonactin | 44.2 | 6.6 | 6.7 |
| Nonactin | 43.4 | 7.0 | 6.2 |
| Dinactin | 46.6 | 7.4 | 6.3 |
| Trinactin | 47.3 | 7.5 | 6.3 |
| Tetranactin | 45.1 | 7.4 | 6.1 |

What is claimed is:

1. A method for promoting the growth of domestic animals characterized by orally administering, to the animals, an effective amount of at least one macrotetrolide antibiotic substance represented by the general formula wherein $R_1$, $R_2$, $R_3$ and $R_4$ each represents a lower alkyl group.

2. A method for promoting the growth of domestic animals according to claim 1, wherein said lower alkyl group is a methyl group or ethyl group.

3. A method for promoting the growth of domestic animals according to claim 1, wherein said macrotetrolide antibiotic substance is selected from the group consisting of nonactin, monactin, dinactin, trinactin and tetranactin.

4. A method for promoting the growth of domestic animals according to claim 1, wherein said macrotetrolide antibiotic substance is polynactin.

5. A method for promoting the growth of domestic animals according to claim 1, wherein said effective amount is 0.01 to 100 mg/day per kg of body weight of the domestic animal.

6. A method for promoting the growth of domestic animals according to claim 1, wherein said macrotetrolide antibiotic substance is orally administered to the animals in the form of a mixture with feed.

7. A method for promoting the growth of domestic animals according to claim 1, wherein said macrotetrolide antibiotic substance is orally administered to the animals in the form of a mixture with feed containing the macrotetrolide antibiotic substance at a concentration of 0.5–1000 ppm.

8. A method for promoting the growth of domestic animals according to claim 1, wherein said domestic animal is a ruminant.

9. A method for promoting the growth of domestic animals according to claim 8, wherein said ruminant is cattle or sheep.

10. A method for promoting the growth of domestic animals according to claim 1, wherein said domestic animal is swine.

* * * * *